United States Patent
Childress

(10) Patent No.: US 9,301,891 B1
(45) Date of Patent: Apr. 5, 2016

(54) WATER RESISTANT PROTECTIVE BODY COVER

(71) Applicant: Dallas Childress, Citrus Heights, CA (US)

(72) Inventor: Dallas Childress, Citrus Heights, CA (US)

(*) Notice: Subject to any disclaimer, the term of this patent is extended or adjusted under 35 U.S.C. 154(b) by 0 days.

(21) Appl. No.: 14/736,968

(22) Filed: Jun. 11, 2015

(51) Int. Cl.
*A41D 13/08* (2006.01)
*A61F 15/00* (2006.01)
*A41D 13/05* (2006.01)
*A41D 27/12* (2006.01)

(52) U.S. Cl.
CPC .......... *A61F 15/004* (2013.01); *A41D 13/0562* (2013.01); *A41D 13/08* (2013.01); *A41D 27/12* (2013.01)

(58) Field of Classification Search
CPC ... A41D 13/0562; A41D 13/08; A41D 27/12; A61F 15/004
USPC ............................. 2/59, 16; 602/13; 128/856
See application file for complete search history.

(56) References Cited

U.S. PATENT DOCUMENTS

| | | | |
|---|---|---|---|
| 5,643,183 A | 7/1997 | Hill | |
| 6,210,352 B1* | 4/2001 | Williams et al. | 602/3 |
| 6,719,711 B1* | 4/2004 | Islava | 602/13 |
| 7,290,290 B2 | 11/2007 | Treadway Fancher | |
| 7,468,048 B2 | 12/2008 | Meehan | |
| 7,559,908 B2* | 7/2009 | Ravikumar | 602/13 |
| 2004/0111789 A1* | 6/2004 | Niki | 2/455 |
| 2010/0094187 A1* | 4/2010 | Murinson | 602/20 |

* cited by examiner

*Primary Examiner* — Katherine Moran
(74) *Attorney, Agent, or Firm* — Crossley Patent Law

(57) ABSTRACT

A water resistant protective body cover including a trapezoidal water resistant cover, an air chamber continuously attached to a top edge of the cover, a hand pump attached to the air chamber, and a pair of interconnectable hook and loop fastener strips including a first strip and a second strip. The first strip is continuously disposed on an exterior surface of a right edge of the cover. The second strip is continuously disposed on an interior surface of a left edge of the cover.

2 Claims, 3 Drawing Sheets

WATER RESISTANT PROTECTIVE BODY COVER

BACKGROUND OF THE INVENTION

Various types of protective body covers are known in the prior art. However, what has been needed is a water resistant protective body cover including a trapezoidal water resistant cover, an air chamber continuously attached to a top edge of the cover, a hand pump attached to the air chamber, and a pair of interconnectable hook and loop fastener strips including a first strip and a second strip. What has been further needed is for the first strip to be continuously disposed on an exterior surface of a right edge of the cover and for the second strip to be continuously disposed on an interior surface of a left edge of the cover. Lastly, what has been needed is for the air chamber to be configured to securely engage around a user's limb when the air chamber is in the inflated position.

The water resistant protective body cover thus allows a user to shower while protecting an affected area from water. The cover can be produced in varying dimensions for use over any part of the user's body.

FIELD OF THE INVENTION

The present invention relates to water resistant body covers, and more particularly, to a water resistant protective body cover.

SUMMARY OF THE INVENTION

The general purpose of the present water resistant protective body cover, described subsequently in greater detail, is to provide a body cover which has many novel features that result in a water resistant protective body cover which is not anticipated, rendered obvious, suggested, or even implied by prior art, either alone or in combination thereof.

To accomplish this, the present water resistant protective body cover includes a trapezoidal water resistant cover, an air chamber, a hand pump, and a pair of interconnectable hook and loop fastener strips. The cover has a right edge, a left edge, a top edge, a bottom edge, an interior surface, and an exterior surface. The cover is optionally a water resistant plastic. The air chamber is continuously attached to the top edge of the cover. The hand pump is attached to the air chamber. The air chamber has an inflated position and an alternate deflated position. The air chamber is configured to securely engage around a user's limb when the air chamber is in the inflated position. The pair of hook and loop fastener strips includes a first strip and a second strip. The first strip is continuously disposed on the exterior surface of the right edge of the cover. The second strip is continuously disposed on the interior surface of the left edge of the cover. The pair of hook and loop fastener strips is configured to secure the right edge of the cover with the left edge of the cover.

Thus has been broadly outlined the more important features of the present water resistant protective body cover so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
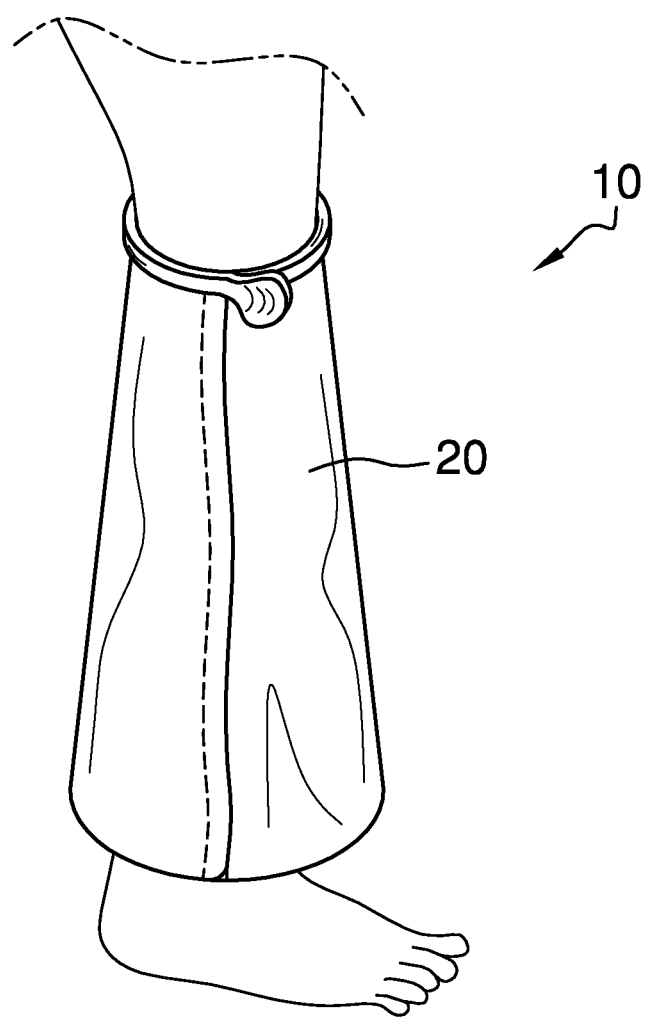
FIG. 1 is an in-use view.
Figure 2:
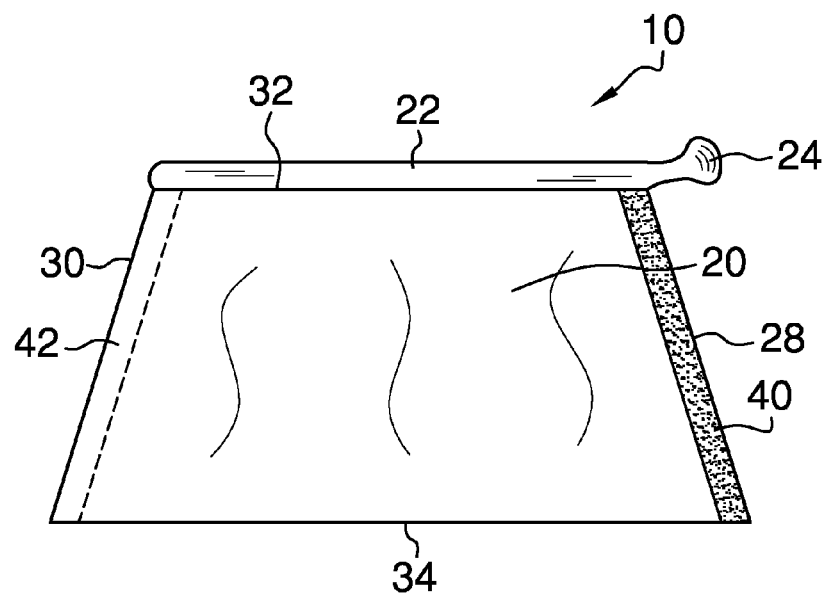
FIG. 2 is a front elevation view.
Figure 3:
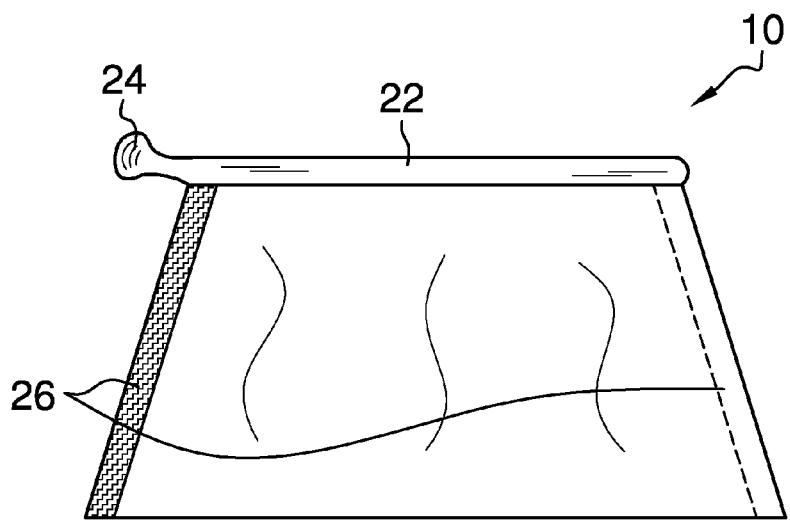
FIG. 3 is a rear elevation view.
Figure 4:
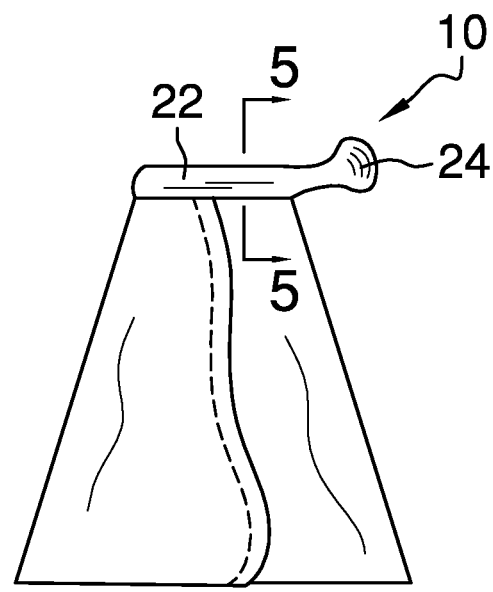
FIG. 4 is a side elevation view.
Figure 5:
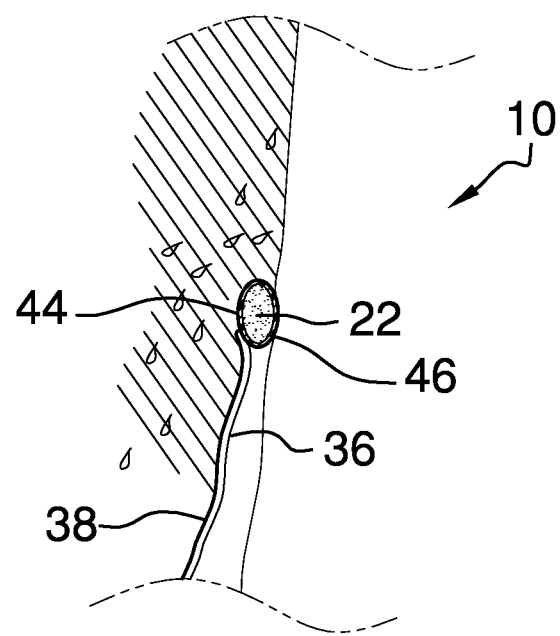
FIG. 5 is a cross-sectional view taken along line 5-5 of FIG. 4.

With reference now to the drawings, and in particular FIGS. 1 through 5 thereof, an example of the instant water resistant protective body cover employing the principles and concepts of the present water resistant protective body cover and generally designated by the reference number 10 will be described.

Referring to FIGS. 1 through 5 the present water resistant protective body cover 10 is illustrated. The water resistant protective body cover 10 includes a trapezoidal water resistant cover 20, substantially tubular closed air chamber 22, a hand pump 24, and a pair of interconnectable hook and loop fastener strips 26. The cover 20 has a right edge 28, a left edge 30, a top edge 32, a bottom edge 34, an interior surface 36, and an exterior surface 38. The air chamber 22 has an external surface 44 and an internal surface 46. A length of the top edge 32 of the cover 20 is continuously attached to the external surface 44 of the air chamber 22. The hand pump 24 is attached to the air chamber 22. The pair of hook and loop fastener strips 26 includes a first strip 40 and a second strip 42. The first strip 40 is continuously disposed on the exterior surface 38 of the right edge 28 of the cover 20. The second strip 42 is continuously disposed on the interior surface 36 of the left edge 30 of the cover 20. The pair of hook and loop fastener strips 26 is configured to secure the right edge 28 of the cover 20 with the left edge 30 of the cover 20.

What is claimed is:
1. A water resistant protective body cover comprising:
   a trapezoidal water resistant cover having a right edge, a left edge, a top edge, a bottom edge, an interior surface, and an exterior surface;
   a substantially tubular closed air chamber having an external surface and an internal surface, wherein a length of the cover top edge is continuously attached to the air chamber external surface;
   a hand pump attached to the air chamber;
   wherein the air chamber has an inflated position and an alternate deflated position;
   wherein the air chamber is configured to securely engage around a user's limb when the air chamber is in the inflated position;
   a pair of interconnectable hook and loop fastener strips comprising a first strip and a second strip, wherein the first strip is continuously disposed on the exterior surface of the cover right edge, and the second strip is continuously disposed on the interior surface of the cover left edge, wherein the pair of hook and loop fastener strips is configured to secure the right edge of the cover with the left edge of the cover.
2. The water resistant protective body cover of claim 1 wherein the cover is a water resistant plastic.

* * * * *